United States Patent [19]

Akatsuka

[11] 4,323,440
[45] Apr. 6, 1982

[54] OXYGEN SENSOR WITH PROTECTIVE SHIELD AND POROUS AIR FILTER

[75] Inventor: Takao Akatsuka, Toyota, Japan

[73] Assignee: Toyota Jidosha Kogyo Kabushiki Kaisha, Aichi, Japan

[21] Appl. No.: 201,237

[22] Filed: Oct. 27, 1980

[30] Foreign Application Priority Data

Mar. 25, 1980 [JP] Japan .................................. 55-38428

[51] Int. Cl.³ ............................................ G01N 27/58
[52] U.S. Cl. .................................................. 204/195 S
[58] Field of Search ............................. 204/195 S, 1 S

[56] References Cited

U.S. PATENT DOCUMENTS

| | | | |
|---|---|---|---|
| 4,057,477 | 11/1977 | Weyl et al. ........................ | 204/195 S |
| 4,088,555 | 5/1978 | Kita et al. ......................... | 204/195 S |
| 4,187,163 | 2/1980 | Steinke et al. .................... | 204/195 S |

*Primary Examiner*—G. L. Kaplan
*Attorney, Agent, or Firm*—Stevens, Davis, Miller & Mosher

[57] ABSTRACT

An oxygen sensor for measuring the existence of oxygen in gases in an exhaust system or the like. An electrolytic body is formed as a tube with an open end and a closed end. An internal electrode is coated on the interior surface of the electrolytic body, and an external electrode is coated on the exterior surface of the electrolytic body. The external electrode is exposed to the gases. A tubular housing is airtightly connected around the outer circumference of the open end of the tubular electrolytic body, thus defining within it an internal space to which the internal electrode is exposed. An electrically conducting tube, coaxial with the tubular housing, is electrically connected to the internal electrode by its end closest thereto. Atmospheric air can only pass into the space within the tubular housing through a side hole in the housing which opposes a side hole in the electrically conducting tube. Between these holes there is located a blocking member which includes a tube formed of an elastomeric material formed with a side hole with corresponds to the other side holes, and a tube formed of a water repellent porous material, the part of which opposes the side holes, and which is not formed with any holes, so that it acts as a filter. One of these tubes is fitted inside the other. A lead wire connects to the other end of the electrically conducting tube and leads out from the sensor to convey electrical output signals therefrom. A protective shield is mounted over the outside of the side hole in the housing, and does not interrupt communication between this hole and the atmosphere, while it shields this hole from direct exposure to the exterior.

6 Claims, 1 Drawing Figure

U.S. Patent
Apr. 6, 1982
4,323,440
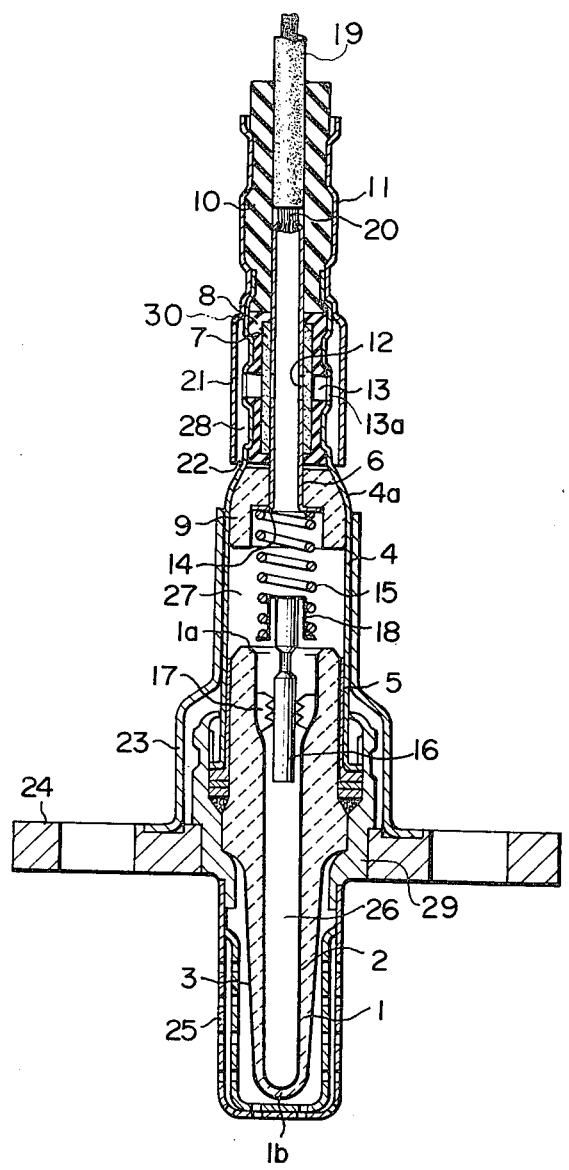

OXYGEN SENSOR WITH PROTECTIVE SHIELD AND POROUS AIR FILTER

BACKGROUND OF THE INVENTION

The present invention relates to an oxygen sensor for detecting the existence of oxygen in a mixture of gases, and, more particularly, relates to an oxygen sensor for detecting the existence of oxygen in the exhaust gases of an internal combustion engine.

Many internal combustion engines at the present time are fitted with 02 sensors for detecting the remainder of oxygen in the exhaust gases emitted by the engine. The signal from such a sensor is used, typically, for controlling the air/fuel ratio of the combustion in the internal combustion engine, or for controlling purification of the exhaust gases of the internal combustion engine by a catalytic converter.

There is a well known form of construction for such a sensor, comprising an electrolytic tubular body made of solid electrolyte such as zirconia, which is formed as a tube open at its one end and closed at its other end, with an internal electrode coated on the interior surface of the electrolytic tubular body, and an external electrode coated on the exterior surface of the electrolytic tubular body. The electrolytic tubular body is protruded into the exhaust passage of the internal combustion engine, so that the external electrode is exposed to the exhaust gases, and atmospheric air is arranged to be provided to the internal electrode. Thereby, a voltage is generated between the external electrode and the internal electrode, which varies according to the proportion of oxygen present in the exhaust gases.

In such an oxygen sensor it is of the greatest importance for attaining accuracy of the output electrical signal produced thereby that a clean and fresh supply of atmospheric air should be provided to the internal space of the electrolytic tubular body, and to the internal electrode. However, it is important also that contaminants such as moisture, oil, dust, dirt, or the like should not be allowed to penetrate to this internal space, since even a small amount thereof may adversely affect the accuracy of the electrical output signal of the sensor. Further, it is very important that splashed-up water, which typically may be scattered over the exhaust system of the automobile when the automobile passes through a puddle or the like, should not penetrate to the interior of the sensor. However heretofore no ideal construction has yet been found for such an oxygen sensor.

SUMMARY OF THE INVENTION

Therefore, it is an object of the present invention to provide a construction for an oxygen sensor which effectively satisfies the above explained requirement for free circulation of atmospheric air to the internal electrode of the sensor, while maintaining a simple strucure which is easy and cheap to manufacture, and yet durable and reliable during use.

It is a further object of the present invention to provide such a construction for an oxygen sensor which effectively ensures that entry of water, dust, dirt, oil, and other contaminants to the interior space within the sensor is effectively prevented.

It is a further object of the present invention to provide such a construction for an oxygen sensor in which splashed-up water is effectively drained from the sensor without any risk that it should penetrate to the interior space therein.

It is yet further object of the present invention to provide an oxygen sensor which provides a stable and reliable electrical output signal which is not adversely affected by the presence of contaminants in the neighbourhood of the sensor.

According to the present invention, these and other objects are attained by an oxygen sensor, comprising (a) an electrolytic body, made of a solid electrolyte material, and formed as a tube with an open end and a closed end; (b) an internal electrode located on the interior end; surface of the tubular electrolytic body; (c) an external electrode located on the exterior surface of the tubular electrolytic body; (d) a tubular housing airtightly connected around the outer circumference of the open end of the tubular electrolytic body, and defining within it an internal space to which the internal electrode is exposed, and formed with a side hole; (e) an electrically conducting tube member, located within the tubular housing and substantially coaxial therewith, and formed with a side hole opposing the side hole in the tubular housing; (f) a blocking member, comprising (fa) a tube formed of water repellent porous material and (fb) a tube made of an elastomeric rubber-like material and formed with a side hole, one of these tubes being within the other, said blocking member being fitted tightly over the electrically conducting tube member and fitting tightly inside the tubular housing and interrupting communication of said internal space within the tubular housing, via the space between the tubular housing and the electrically conducting tube member, to the outside, with said side hole in the tube which is made of an elastomeric rubber-like material corresponding to the side holes in the tubular housing and in the electrically conducting tube member; (g) a means for electrically connecting the internal electrode with the end of the electrically conducting tube member closest thereto; (h) a lead wire connected to the other end of the electrically conducting tube member and leading to the outside of the sensor, communication between said internal space within the tubular housing via the part of the inside of the electrically conducting tube member closer to said other end thereof than said blocking member to the outside being interrupted; and (i) a protective shield located over the outside of the side hole in the housing, which does not interrupt communication between said side hole and the atmosphere, but which shields said side hole from direct exposure to the exterior.

According to such a construction, since the portion of the tube made of water repellent porous material which is between the hole in the electrically conducting tube and the hole in the tubular housing is not pierced with any hole, it functions as a filter for preventing the ingress of water, oil or other contaminants into the interior space within the sensor to which the internal electrode is exposed. Further, by the provision of the protective shield member covering the side hole in the housing, although communication between the side hole and the atmosphere is not interrupted by this shield member, since the shield protects the side hole from direct exposure to the exterior, water which is splashed against the sensor, or oil which is dripped thereon, or dust which is blown thereon, or the like, are prevented from entering through the hole in the housing to reach the interior of the sensor and disturb the electrical output signal produced thereby.

Further, according to a particular aspect of the present invention, the protective shield may be a tubular member provided around the tubular housing and may be joined to the tubular housing at its one axial end, an annular space being defined between the protective shield and the tubular housing, and a drain hole may be bored through the protective shield proximate to said connecting portion thereof.

However, if the sensor is mounted in a position in which the closed end of the tubular protective shield joined to the tubular housing is higher than the open end thereof, the drain hole may be ommitted. On the other hand, as aparticular modification, this drain hole may be provided as a plurality of holes all around the sensor, to ensure the draining action by the drain hole when the sensor is mounted in various different rotational positions, around its central axis, with the open end of the tubular protective shield being positioned higher than the closed end thereof.

BRIEF DESCRIPTION OF THE DRAWING

The present invention will now be shown and described with reference to several preferred embodiments thereof, and with reference to the illustrative drawing. It should be clearly understood, however, that the description of the embodiments, and the drawing, are all of them given purely for the purposes of explanation and exemplification only, and are none of them intended to be limitative of the scope of the present invention in any way, since the scope of the present invention is to be defined solely by the legitimate and proper scope of the appended claims.

In the drawing, the sole FIGURE is a vertical part cross-sectional view taken along the central axis of an oxygen sensor which is a first preferred embodiment of the present invention, showing the internal parts thereof.

DESCRIPTION OF THE PREFERRED EMBODIMENTS

In the O2 sensor shown in part sectional view in the drawing, a tubular electrolytic body member 1 is formed of an electrolytic solid material such as zirconia, and is shaped as a tube, which is open at its open end 1a, uppermost in the drawing, and is closed at its closed end 1b, lowermost in the drawing. An internal electrode 2 is formed as a thin layer of electrically conducting material which is coated on the inner surface of the electrolytic body member 1, and similarly an external electrode 3 is formed as a thin layer of electrically conducting material which is coated on the outer surface of the electrolytic body member 1.

Around the external circumference of the open end 1a of the electrolytic body member 1 there is connected, in an airtight manner, a tubular housing 4. The housing 4 extends in the direction away from the closed end 1b of the electrolytic body member 1. In the embodiment shown in the drawing, an intermediate tubular member 5 is mounted between the interior surface of the end of the tubular housing 4 which engages to the external circumference of the open end 1a of the electrolytic body member 1, and this external circumference, for effectively promoting this airtight seal.

Inside and coaxial with the tubular housing 4, in its upper portion in the drawing, there is disposed an electrically conducting tube member 6, and, in the embodiment shown in the drawing, the lower end of the tube member 6 is supported within the tubular housing 4 by an insulating material ring 9, while, between the upper end of the tube member 6, and the upper end of the tubular housing 4 and also an upper tubular housing 11 which will be described later, there is fitted a mounting tube 10 made of an elastomeric material such as rubber. Thereby, the tube member 6 is firmly supported with respect to the tubular housing 4.

At the lower end in the drawing of the tube member 6 there is formed an end flange 14, which is located within a recess on the lower end of the insulating material ring 9, and seated within this recess against the end flange 14 there rests the upper end of a compression coil spring 15. This compression coil spring 15 is under compression, and its lower end is seated on a cap member 18. The cap member 18 is impelled downwards in the drawing by the compression coil spring 15 against the upper end of an electrode connecting member 16, the lower end of which is clamped by a crimp member 17 which is mounted on the inner surface of the internal electrode 2. According to this structure, the internal electrode 2 is electrically connected via the crimp member 17, the connecting member 16, the cap member 18, the compression coil spring 15, and the end flange 14 to the tube member 6. The upper end in the drawing of the tube member 6 is connected by soldering or the like to the central wire 20 of an electrical lead cable 19, which leads upwards in the drawing so as to conduct electrical signals from the sensor.

In the shown embodiment, the tubular housing 4 is continued upwards by an upper tubular housing 11, and within this housing 11 there is tightly received the upper part of the mounting tube 10. By the upper tubular housing 11 squeezing the mounting tube 10 against the outer surface of the electrical lead cable 19, communication of the internal space within the upper part of the tube member 6 to the atmosphere, upwards in the drawing through the central hole of the upper tubular housing 11, is effectively cut off.

Thus the internal space 26 which is defined within the electrolytic body member 1 is communicated past the crimp member 17, which does not form a sealing engagement with the electrode connecting member 16, upwards in the drawing to the internal space 27 defined within the intermediate part of the tubular housing 4, and this internal space 27 is communicated to the internal space within the tube member 6. This internal space within the tube member 6 is not directly communicated in the upward direction in the drawing to the atmosphere. However, in the side of the tube member 6 there is pierced a tube hole 12, and opposing this tube hole 12 there is pierced a housing hole 13a in the side of the tubular housing 4.

Between this part of the outer surface of the tube member 6 and the inner surface of the tubular housing 4 there is mounted a mounting tube 8, which is formed of an elastomeric material such as rubber, and which is formed with a mounting tube hole 13 which corresponds to the tube hole 12 and the housing hole 13a. Further, squeezed between the mounting tube 8 and the outer surface of the tube member 6 there is mounted a filter tube 7, which is formed from a porous material such as tetrafluorethylene, which has a porosity of approximately 50%. No hole is formed in this filter tube 7 in its portion corresponding to the tube hole 12, the mounting tube hole 13 and the housing hole 13a. Thus, the assembly of the filter tube 7 and the mounting tube 8 together forms a blocking member, which provides a certain filtering action for air passing through the housing hole 13a and the tube hole 12 to the internal space within the tube member 6, but which does not intercept completely passing of this air.

Around the upper part of the tubular housing 4, over the housing hole 13a therein, there is mounted a protective shield 21, which, in this embodiment, is formed as an extension of the upper tubular housing 11. Between the lower end of the protective shield 21, and the tapered lower end portion 4a of the tubular housing 4, there is present an annular gap 22. The internal diameter of the protective shield 21 is somewhat greater than the external diameter of the tubular housing 4 in the region of the housing hole 13a, so that the exterior of the housing hole 13a is communicated to the atmosphere via the annular gap 22. Accordingly, communication of the internal space 26 within the electrolytic body member 1 to the atmosphere is possible, via the internal space 27, the internal hole within the tube member 6, the tube hole 12, through the porosities in the filter tube 7, and through the mounting tube hole 13 and the housing hole 13a to the internal space 28 within the protective shield 21, and through the annular gap 22. However, the housing hole 13a is not directly exposed to the exterior, because of the shielding effect of the protective shield 21.

On the external surface of the tubular housing 4 there is mounted an outer tubular housing body 23, and to the lower flanged end in the drawing of the outer tubular housing body 23 there is mounted a mounting flange member 24, which is pierced with holes therein for mounting the 02 sensor as a whole to the exhaust manifold of an automobile or the like. A mounting block 29 is provided between the tubular electrolytic body member 1 and the mounting flange member 24. Further, around the closed end 1b of the electrolytic body member 1 there is mounted a protective cover 25, which in this embodiment is formed as a double skinned member. The protective cover 25 is pierced with a number of holes therein for allowing free access of exhaust gas to the external electrode 3 on the electrolytic body member 1.

According to the operation of the 02 sensor shown in the FIGURE, when it is bolted to the exhaust manifold of an internal combustion engine, exhaust gases of the engine circulate freely through the small holes in the protective cover 25 to impinge on the external electrode 3 on the outside surface of the electrolytic body member 1. At the same time, atmospheric air enters via the annular gap 22, the internal space 28, the mounting tube hole 13, the housing hole 13a, through the porosities in the filter tube 7, and through the tube hole 12 to the interior space within the sensor, and thus impinges on the internal electrode 2 on the inner surface of the electrolytic body member 1. According, therefore, to the well known operation of such a sensor, a voltage potential is generated between the external electrode 3 and the internal electrode 2. The external electrode 3 is earthed to the ground of the automobile via the mounting block 29, the mounting flange member 24, etc., while the electrical signal relative to this earth produced on the internal electrode 2 is conducted, via the crimp member 17, the electrode connecting member 16, the compression coil spring 15, the tube member 6, etc., to the central wire 20 of the electrical lead cable 19, and is conducted thereby to a control mechanism for the automobile such as an exhaust gas recirculation system. Good circulation of relatively pure atmospheric air to the internal space 26 within the electrolytic body member 1, which is essential for proper operation of the sensor, is assured, while at the same time entry of noxious contaminants to the interior space within the sensor is prevented by the filtering action of the filter tube 7. Further, splashing of water, oil, dirt, or the like, onto the outside of the filter tube 7 is effectively prevented by the provision of the protective shield 21.

Various possible modifications may be made to the sensor of the present invention, as alterations of the design shown in the FIGURE. For example, in order to improve circulation of air to the interior of the sensor, one or more small holes may be provided in the protective shield 21, as long as they are not opposed to the housing hole 13a in the tubular housing 4, for improving entry of air to the internal space 28 within the protective shield 21. Further, it is not necessary to provide the protective shield 21 as a circular member completely surrounding the upper portion of the tubular housing 4. Further, as an advantageous modification, one or more small holes, such as a hole 30 shown in phantom lines in the drawing, may be drilled through the protective shield 21 at its upper part, where it joins onto the tubular housing 4. These are very useful when the sensor is mounted in the automobile in a position in which its upper part in the drawing is at a lower elevation than its lower part in the drawing, so that there is a risk of splashed up water being trapped within the 28 formed between the protective shield 21 and the tubular housing 4. Such holes serve to drain positively such trapped water. If such holes extend all around the circumference of the protective shield 21, then they will be able to drain trapped water, no matter in what rotational orientation the sensor is mounted about its central axis.

As yet another possible modification, it would be quite within the scope of the present invention for the relative positons of the mounting tube 8 and the filter tube 7 to be interchanged. In other words, although in the shown embodiment the mounting tube 8 is shown as fitting over the outside of the filter tube 7, in an alternative embodiment the filter tube 7 could be fitted over the outside of the mounting tube 8.

Although the present invention has been shown and described with reference to several preferred embodiments thereof, and in terms of the illustrative drawing, it should not be considered as limited thereby. Various possible modifications, omissions, and alternations could be conceived of by one skilled in the art to the form and the content of any particular embodiment, without departing from the scope of the present invention. Therefore it is desired that the scope of the present invention, and of the protection sought to be granted by Letters Patent, should be defined not by any of the perhaps purely fortuitous details of the shown embodiments, or of the drawing, but solely by the scope of the appended claims, which follow.

I claim:
1. An oxygen sensor, comprising:
(a) an electrolytic body, made of a solid electrolyte material, and formed as a tube with an open end and a closed end;
an internal electrode located on the interior surface of the tubular electrolytic body;
(c) an external electrode located on the exterior surface of the tubular electrolytic body;
(d) a tubular housing airtightly connected around the outer circumference of the open end of the tubular electrolytic body, and defining within it an internal space to which the internal electrode is exposed, and formed with a side hole;

(e) an electrically conducting tube member, located within the tubular housing and substantially coaxial therewith, and formed with a side hole opposing the side hole in the tubular housing;

(f) a blocking member, comprising (fa) a tube formed of water repellent porous material and (fb) a tube made of an elastomeric rubber-like material and formed with a side hole, one of these tubes being within the other, said blocking member being fitted tightly over the electrically conducting tube member and fitting tightly inside the tubular housing and interrupting communication of said internal space within the tubular housing, via the space between the tubular housing and the electrically conducting tube member, to the outside, with said side hole in the tube which is made of an elastomeric rubber-like material corresponding to the side holes in the tubular housing and in the electrically conducting tube member;

(g) a means for electrically connecting the internal electrode with the end of the electrically conducting tube member closest thereto;

(h) a lead wire connected to the other end of the electrically conducting tube member and leading to the outside of the sensor, communication between said internal space within the tubular housing via the part of the inside of the electrically conducting tube member closer to said other end thereof than said blocking member to the outside being interrupted; and (i) a protective shield located over the outside of the said hole in the housing, which does not interrupt communication between said side hole and the atmosphere, but which shields said side hole from direct exposure to the exterior.

2. A sensor according to claim 1, wherein the protective shield is a tubular member provided around the tubular housing and is joined to the tubular housing at its one axial end to the electrolytic body, an annular space being defined between the protective shield and the tubular housing.

3. A sensor according to claim 2, wherein a drain hole is bored through the protective shield proximate to said connecting end thereof, whereby fluid may be drained from said annular space when the sensor is in an orientation with the open end of the protective shield higher than the connecting end.

4. A sensor according to claim 2, wherein a plurality of drain holes are bored through the protective shield all around said connecting portion thereof, whereby fluid may be drained from said annular space when the sensor is in an orientation with the electrolytic body higher than said connecting portion, no matter what be the orientation of the sensor around its central axis.

5. A sensor according to claim 1, further comprising an elastic sealing member which is clamped between the part of said tubular housing remote from the electrolytic body and the outer surface of said lead wire, whereby the end of said sensor is sealed in order to prevent passage of air therethrough.

6. A sensor according to claim 1, wherein the tube formed of elastomeric rubber-like material is outside the tube formed of water repellent porous material.

* * * * *